United States Patent
Veil et al.

(10) Patent No.: US 11,090,476 B2
(45) Date of Patent: Aug. 17, 2021

(54) NEEDLE-GUIDING DEVICE FOR A SKIN PRICKING DEVICE AND SKIN PRICKING DEVICE

(71) Applicant: MT.DERM GmbH, Berlin (DE)

(72) Inventors: Tobias Veil, Berlin (DE); Andy Holland, Berlin (DE)

(73) Assignee: MT.DERM GMBH, Berlin (DE)

( * ) Notice: Subject to any disclaimer, the term of this patent is extended or adjusted under 35 U.S.C. 154(b) by 42 days.

(21) Appl. No.: 16/325,340

(22) PCT Filed: Jun. 7, 2018

(86) PCT No.: PCT/EP2018/064962
§ 371 (c)(1),
(2) Date: Feb. 13, 2019

(87) PCT Pub. No.: WO2018/228902
PCT Pub. Date: Dec. 20, 2018

(65) Prior Publication Data
US 2019/0209823 A1   Jul. 11, 2019

(30) Foreign Application Priority Data
Jun. 12, 2017   (EP) ..................................... 17175471

(51) Int. Cl.
*A61M 37/00*   (2006.01)
(52) U.S. Cl.
CPC ................ *A61M 37/0076* (2013.01)
(58) Field of Classification Search
CPC .......... A61M 37/0076; A61M 37/0084; A61B 2017/3405; A61B 2017/00769;
(Continued)

(56) References Cited

U.S. PATENT DOCUMENTS

| 2005/0066775 | A1 | 3/2005 | Chen |
| 2014/0358172 | A1* | 12/2014 | Lin ................... A61M 37/0076 606/185 |
| 2016/0067739 | A1* | 3/2016 | Jones .................. A61M 5/3287 604/507 |

FOREIGN PATENT DOCUMENTS

| CN | 2 517 389 | 10/2002 |
| DE | 299 19 199 | 1/2000 |

(Continued)

*Primary Examiner* — George J Ulsh
*Assistant Examiner* — Andrew P. Restaino
(74) *Attorney, Agent, or Firm* — Leason Ellis LLP

(57) ABSTRACT

The disclosure relates to a needle-guiding device for a skin pricking device, comprising a base body, a skin pricking needle (3) and a needle channel (14), which is formed in the base body and in which the skin pricking needle (3) is arranged, wherein the skin pricking needle (3) can be moved back and forth repeatedly in the needle channel (14) along a movement path, wherein a channel wall (17) of the needle channel (14) has proximal guide wall sections (18) with respect to the skin pricking needle (3), on which the skin pricking needle (3) comes to rest for the needle guidance in response to the back and forth movement, and has distal wall sections (19), which are recessed relative to the proximal guide wall sections (18) and which are free from a direct contact with the skin pricking needle (3) in response to moving the skin pricking needle (3) back and forth in the needle channel (14). A skin pricker is furthermore provided.

14 Claims, 20 Drawing Sheets

(58) Field of Classification Search
CPC . A61B 2017/349; A61B 17/205; A61B 17/34; A01K 11/005
See application file for complete search history.

(56) References Cited

FOREIGN PATENT DOCUMENTS

| | | | |
|---|---|---|---|
| DE | 10 2014 011 438 | 2/2016 | |
| EP | 1 495 782 | 1/2005 | |
| JP | 2008 125830 | 6/2008 | |
| JP | 2008125830 A * | 6/2008 | ........ A61M 37/0076 |

* cited by examiner

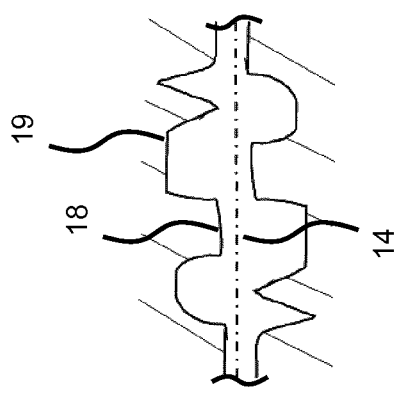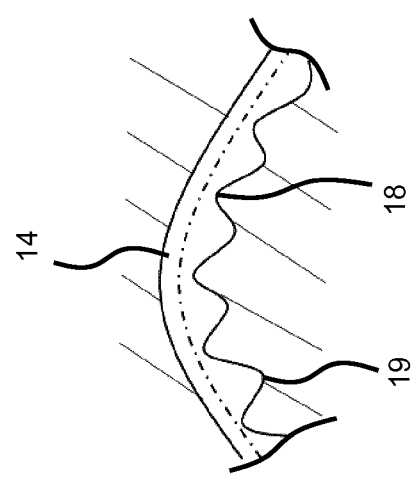
Fig. 16

NEEDLE-GUIDING DEVICE FOR A SKIN PRICKING DEVICE AND SKIN PRICKING DEVICE

CROSS-REFERENCE TO RELATED PATENT APPLICATIONS

This application is a U.S. National Phase Application under 35 U.S.C. § 371 of International Patent Application No. PCT/EP2018/064962, filed Jun. 7, 2018, which claims the priority of European Application No. 17 175 471.6, filed Jun. 12, 2017, which is incorporated by reference as if expressly set forth in its entirety herein.

The present disclosure relates to a needle-guiding device for a skin pricking device and to a skin pricking device for puncturing or piercing a human or animal skin.

BACKGROUND

Skin pricking devices or skin prickers, thus devices for locally puncturing a human or an animal skin, are usually designed as hand-held devices. The operating personnel can use such hand-held devices to apply an ink for a tattoo and/or permanent make-up in the area of the skin surface. However, the introduction of cosmetic or medicinal substances via the skin is possible by means of such devices, in that the skin is locally punctured. Such devices can furthermore be used without any substance being introduced, for example for the skin stimulation.

A hand-held device for locally puncturing a skin is known for example from the publication DE 299 19 199 U1. The known hand-held device has a handle, a drive mechanism and a pricking needle, which is moved back and forth with the help of the drive mechanism relative to a needle nozzle during operation, wherein at least two modules are provided, which are releasably connected to one another, and the one of the two modules is formed as reusable basic module comprising an integrated drive mechanism. The other one of the two modules is a sterilized disposable module, into which all of the components, which can be infected by the bodily fluids of a customer, are integrated in the case of the known hand-held device. The hand-held device is made available in this way in the form of two modules, one of which, namely the disposable module, can be replaced after the use, while the other module, which comprises the drive mechanism, is reused. The hygienic conditions in response to applying a tattoo and/or of permanent make-up are improved with the help of the disposable module, because all parts, which can potentially be contaminated by the bodily fluid of the customer escaping in response to the treatment, are replaced. It is thus avoided that the entire hand-held device needs to be replaced.

A drive module for a device for locally puncturing a human or an animal skin is known from document EP 1 495 782 A1, in which a drive mechanism, by means of which a drive movement can be created, and a conversion mechanism, which is coupled to the drive mechanism and by means of which the rotational drive movement is converted into a forward/backward movement, which can be coupled into a pricker, which locally punctures the skin, so that a repetitive movement of a skin pricking needle is made possible. The conversion mechanism comprises a functional component, which performs a tumbling or tilting movement in response to the movement conversion, whereby a drive force for moving a needle, which locally punctures the skin, is provided in forward and backward direction.

In the case of known devices, the skin pricking needle is received in a needle module, which couples to the drive module in order to couple the provided drive movement or force for back and forth movement to the skin pricking needle, which is guided in the needle module in response to this movement.

An anti-splash needle mounting structure is known from document US 2014/0358172 A1, which includes a grip portion comprising a receiving space for receiving a tattoo needle-drive mechanism and an opening at a bottom end of the handle portion in communication with the receiving space, so that a tattoo needle of the tattoo needle drive mechanism can be exposed outside the opening. The needle mounting structure furthermore includes a tattoo needle-guiding tube comprising two ends, each provided with two through holes, and an outer periphery of the top end comprising a second connecting unit configured for connection with a first connecting unit, which is provided in an inner periphery of the opening. The two through holes are in communication with each other and the inner wall of the tattoo needle-guiding tube is axially formed with a plurality of grooves each having two ends, which each extend to the two through holes.

A tattoo needle for tattooing the skin with colorant is known from the document DE 10 2014 011 438 A1, comprising a needle body, which extends along a longitudinal axis running in the longitudinal direction and which tapers off in a taper in the longitudinal direction at least at one end, in particular in a tip, which is formed to at least partially insert the tattoo needle into the skin, wherein the tattoo needle is formed to be able to guide the colorant along at least a part of the surface. For the improved color transfer, at least one relief is provided in order to be able to receive, in particular store, a part of the colorant therein, wherein the relief is introduced into the surface as recess and extends at least partially perpendicular to the longitudinal axis.

A tattoo needle for injecting a liquid is known from document JP 2008-125830 A, which is formed with a liquid flow guide groove on the surface of an inclined section of the tattoo needle. The liquid flow guide groove is preferably oriented parallel to the axis of the tattoo needle, the liquid flow guide groove is a spiral groove inclined towards the axis of the tattoo needle, and in a case, in which the liquid flow guide groove is a spiral groove and inclined towards the axis of the tattoo needle, the tattoo needle injects the liquid into the grooves, so that a plurality of spiral grooves cross.

SUMMARY

It is the object of the present disclosure to provide a needle-guiding device for a skin pricking device and a skin pricking device, by means of which an improved guidance is provided for the pricking needle.

To solve the object, a needle-guiding device for a skin pricking device as well as a skin pricking device according to the independent claims 1 and 15 are created. Further embodiments are the subject matter of dependent subclaims.

According to one aspect, a needle-guiding device for a skin pricking device is provided, which has a base body and a pricking or skin pricking needle, as well as a needle channel, which is formed in the base body and in which the skin pricking needle is arranged. The skin pricking needle can be moved back and forth repeatedly in the needle channel along a movement path. Along the movement path, a channel wall of the needle channel has proximal guide wall sections with respect to the skin pricking needle, on which the skin pricking needle comes to rest for the needle guidance in response to the back and forth movement, and has distal wall sections, which are recessed relative to the proximal guide wall sections and which are free from a direct contact with the skin pricking needle in response to moving the skin pricking needle back and forth in the needle channel.

According to a further aspect, a skin pricker or skin pricking device comprising a drive module and a needle module coupled thereto is provided, wherein the needle module has a needle-guiding device of the above-mentioned type.

The base body can be designed in one or multiple part. For example, a one- or multiple part housing can be provided, for example a housing comprising housing cover.

The skin pricking needle can be designed as an individual needle or as a needle group, in which a plurality of individual needles are combined to form the skin pricking needle. The individual needle(s) can have a round or a flat profile in the cross section.

Skin prickers or skin pricking device, in particular in the form of hand-held devices, comprising a drive module and a needle module coupled thereto are known as such in different embodiments. For example, the drive module can provide a repetitive drive movement, wherein an electric motor can be used as drive. The drive movement is transferred to a needle shaft in the needle module via a coupling mechanism, in order to move the skin pricking needle received on the needle shaft back and forth, wherein, at least in an extended position, a needle tip of the skin pricking needle is arranged outside of a front-side opening of the needle module, which is also referred to as needle opening. The needle opening can be formed on a needle nozzle, which is arranged on the front side of the needle module, for example as releasable and thus replaceable needle nozzle. It can be provided that the drive mechanism is set up to provide a drive movement with a repetition frequency of between approximately 30 Hz and approximately 160 Hz during operation.

The skin pricker can be formed as a hand-held device, in the case of which a handle is formed on the housing.

The needle module comprising the needle-guiding device can be formed as disposable module, which is releasably attached to the drive module.

In the case of the design with changeable module or needle nozzle, it can be provided that identical module or needle nozzles or different module or needle nozzles are used with one and the same needle module. A module or needle nozzle can consist of different materials, for example plastic and/or metal. A design as injection molded part can be provided. The module or needle nozzle can be formed in one or multiple parts, for example with the help of a plurality of nozzle components, which can be interconnected.

The needle-guiding device can be formed completely or partially in the module or needle nozzle.

The proximal guide wall sections and the distal wall sections can be formed alternately along the movement path in the needle channel. A distal wall section can hereby always follow a proximal guide wall section, and vice versa. In the alternative, a plurality of proximal guide wall sections can also be formed between a plurality of distal wall sections.

The formation of the proximal guide wall sections and of the distal wall sections can be limited to a partial area of a periphery of the channel wall encompassing the needle channel. For example, the proximal guide wall sections and the distal wall sections can be formed only on two opposite sides of the needle channel, whereas wall sections of the channel wall located opposite one another, the imaginary connecting line of which is placed at right angles thereto, do not have such a structuring, are formed for example to be flat or planar. In combination with a skin pricking needle, which has a flat profile in the cross section, it can thus be provided that the proximal guide wall sections and the distal wall sections are formed only in areas of the channel wall, which are located opposite the flat front and/or the flat rear side of the skin pricking needle.

The proximal guide wall sections and/or the distal wall sections can be arranged along one or a plurality of spiral lines each running around the needle channel. The spiral line can be designed as helical line, thus a spiral line with consistent incline. A plurality of spiral or helical lines can hereby be provided, which are each assigned to a proximal guide wall section or to a distal wall section. In the case of this embodiment, the structuring of the channel wall comprising the proximal guide wall sections and the distal wall sections preferably extends completely around the skin pricking needle.

In another embodiment, the proximal guide wall sections and/or the distal wall sections can alternatively or additionally be arranged along one or a plurality of lines, which are curved in a meander-like manner, along the needle channel.

The needle channel can be designed as a fluid-transporting channel. In the case of this embodiment, the needle channel is additionally set up as fluid-transporting channel, in order to transport a fluid to be introduced into the skin, for example an ink, from a channel inlet of the needle channel to a channel outlet of the needle channel in response to moving the skin pricking needle back and forth. This can take place for example in that the fluid is transported towards the channel outlet piece by piece in response to moving the skin pricking needle back and forth, in that the needle movement transfers the fluid between adjacent volumes, which, in the area of the distal wall sections, are upstream of the latter. The fluid is transported forward piece by piece along the movement path in this way, so as to finally reach the channel outlet.

Volumes upstream of the distal wall sections can be in fluid communication along the movement path. In the case of this design, the transport of the fluid takes place along the fluid-transporting channel, in that the fluid flows between the adjacent volumes. The transport caused by the movement of the skin pricking needle can act additionally. A continuous fluid connection between the channel inlet and the channel outlet can be formed. The fluid can be transported for example along distal wall sections, which extend along a spiral encompassing the movement path.

The movement path can have a straight section in a straight needle channel section and/or a curved section in a curved needle channel section. The movement path in the needle channel can be formed completely straight or completely curved. The respective movement path can be set up to move the skin pricking needle parallel or obliquely to the longitudinal direction of the base body comprising the needle channel in response to exiting from a needle-guiding nozzle.

The proximal guide wall sections can have a flat and/or a punctiform contact surface such that, in response to guiding the skin pricking needle in the needle channel, said skin pricking needle forms a flat and/or a punctiform direct contact with the proximal guide wall section. The flat contact surface can run along a linear contact surface. The different contact surfaces can be formed on proximal guide wall sections, which have a triangular or quadrangular cross section. A rounded surface facing the skin pricking needle in the area of the proximal guide wall section can also be provided. All of the contact surfaces formed in the needle channel can be designed to be identical or different. The contact surfaces of proximal guide wall sections arranged adjacently to one another and/or opposite one another can differ hereby. In the different designs, the proximal guide wall sections and the distal wall sections can be formed along a wave-shaped channel wall, wherein the wave peaks and wave troughs can be formed comparable to a sinusoidal wave or a triangle wave.

The proximal guide wall sections and/or the distal wall sections can be formed offset to one another in channel wall sections located opposite one another along the movement path. In one embodiment, a serpentine needle channel can be formed.

The needle channel can be connected to a fluid reservoir. The connection to the fluid reservoir can couple to the needle channel on the rear side of a needle nozzle. The fluid reservoir can be arranged in the needle module itself.

An effective channel width of the needle channel, which is determined by a distance at right angles to the longitudinal direction of the needle channel of proximal guide wall sections on opposite sides of the needle channel, can be larger than a thickness of the skin pricking needle, in particular such that a smooth moving of the skin pricking needle in the needle channel is at hand, in particular also when the fluid is transported along the needle channel. The effective channel width can be consistent across the length of the needle channel. In the alternative, the effective channel width can change over the length of the needle channel. The needle nozzle can be provided on a needle module, which is releasably coupled to a drive module of a hand-held device for locally piercing a human or animal skin. The channel outlet can form the outlet opening at a tip of the needle module.

The effective needle channel width (effective needle channel diameter) can be smaller than the width (the diameter) of a minimal discharge volume, which is determined by a minimal distance at right angles to the longitudinal direction of the needle channel of proximal guide wall sections and opposite distal wall sections. It can thereby be made possible to regulate the flow of the fluid to be discharged, for example an ink, via the setting of the width (of the diameter) of the discharge volume, and to simultaneously provide a precise needle guidance through a narrow effective needle channel width. A precise/tight guidance of the skin pricking needle with simultaneous "high" fluid flow can thus be attained.

The needle channel can at least partially be formed in a needle nozzle.

The needle channel can at least partially be formed in a needle-guiding component of a needle module for a skin pricker. The needle-guiding component can be arranged rearwards of the module tip with the needle opening of the needle module in the housing of the needle module, for example such that an exposed section of the skin pricking needle, which is not arranged in a needle-guiding channel, is formed in the area of the module tip between the channel outlet on the needle-guiding component and a guide of the skin pricking needle. The needle-guiding component can be arranged in the housing of the needle module as releasable component.

The base body can be designed as a disposable component with the needle channel. Such a design can for example be provided in connection with a replaceable needle or module nozzle.

In an alternative embodiment of the needle nozzle, a needle-guiding element can be arranged in the area of the needle opening, which needle-guiding element is designed for example as attachment or top piece and in which the skin pricking needle is guided in an extension of the needle channel in response to moving forward and backward. The needle-guiding element can stick out from the needle nozzle and can be inserted or plugged into the needle opening with a proximal end. In the alternative, the proximal end can be attached to the needle-guiding element or can be integrally molded to the needle nozzle. An outlet opening for the skin pricking needle can thus be arranged offset to the needle opening. The needle-guiding element can be formed free from proximal guide wall sections and distal wall sections.

In a further alternative embodiment of the needle nozzle, a needle-guiding element, which is designed as attachment piece, insert or top piece and in which the skin pricking needle is guided in the needle channel in response to moving forward and backward, can be arranged in the area of the needle opening. The needle-guiding element can stick out to the front or protrude from the needle nozzle and can be inserted into the needle opening with a proximal end. In the alternative, the needle-guiding element can be attached. A one-piece design with the needle nozzle can be provided as well. In the area of the channel wall, the proximal guide wall sections and the distal wall sections can be formed along the needle channel on the needle-guiding element. An outlet opening for the skin pricking needle can be arranged offset to (upstream of) the needle opening. A guide section, which connects to the needle-guiding element, can be arranged on the rear side in the section comprising the needle opening. In the alternative, a distance can be provided therebetween.

DESCRIPTION OF EXEMPLARY EMBODIMENTS

Exemplary embodiments will be described below with reference to Figures of a drawing, in which FIG. 1 shows a schematic illustration of a skin pricker designed as hand-held device for locally piercing a human or an animal skin, for example for creating a tattoo or permanent make-up;

FIG. 16 shows schematic illustrations for further embodiments of a needle channel;

Figure 1:
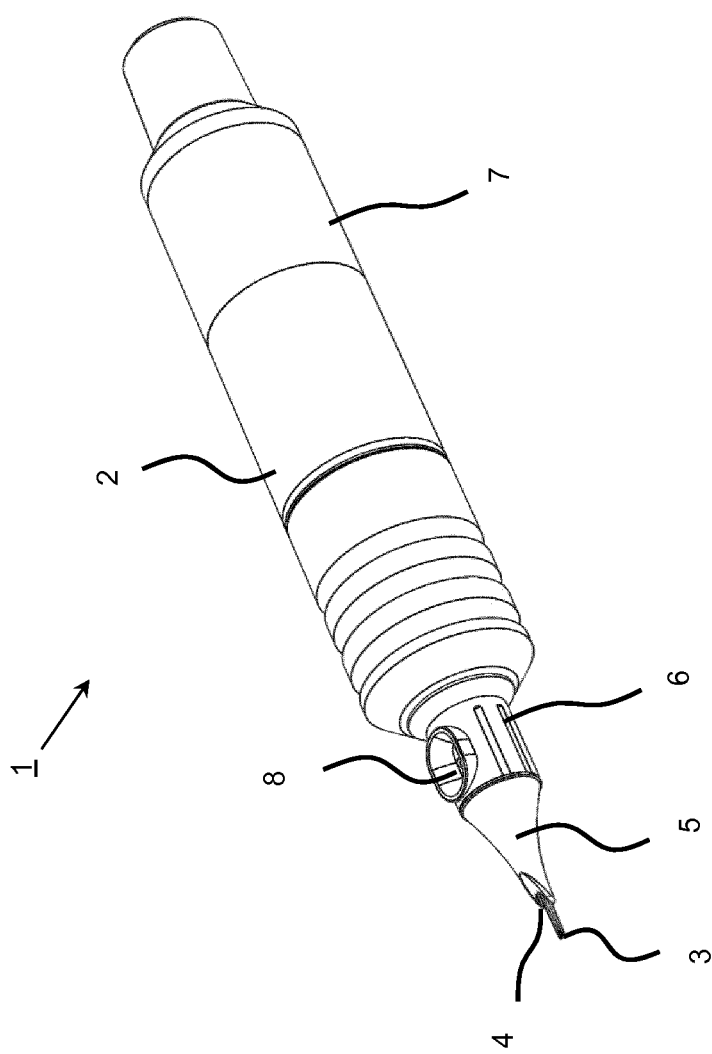

FIG. 1 shows a perspective illustration of a skin pricker or skin pricking device 1 designed as hand-held device, which is formed modularly. A drive mechanism as well as a coupling mechanism (not illustrated) are received in a housing 2, which is designed modularly or in multiple parts here, by means of which a drive force generated by the drive mechanism, for example an electric motor, is coupled to a pricker, which, in the case of the illustrated embodiment, is designed with a pricking or skin pricking needle 3, which has a needle group. The skin pricking needle 3 is shown in an extended position in FIG. 1. In the extended position, the skin pricking needle 3 protrudes beyond a needle opening 4 on a needle nozzle 5 of a needle module 6. The needle module 6 couples to a drive module 7, which has the drive mechanism in the housing 2. The skin pricker 1 can be combined with a controller (not illustrated), in order to supply the drive mechanism with energy during operation and in order to control the pricking movements, thus the extension and retraction of the pricking needle 3.

A fluid to be introduced, for example an ink or a medicinal or cosmetic substance, can be introduced via an opening 8, in order to then discharging the fluid via the needle or needle nozzle opening 4 to the skin. In the alternative or in addition, a fluid reservoir (not illustrated), which is in fluid communication with the needle opening 4, can be provided in and/or on the housing 2.

Figure 2:
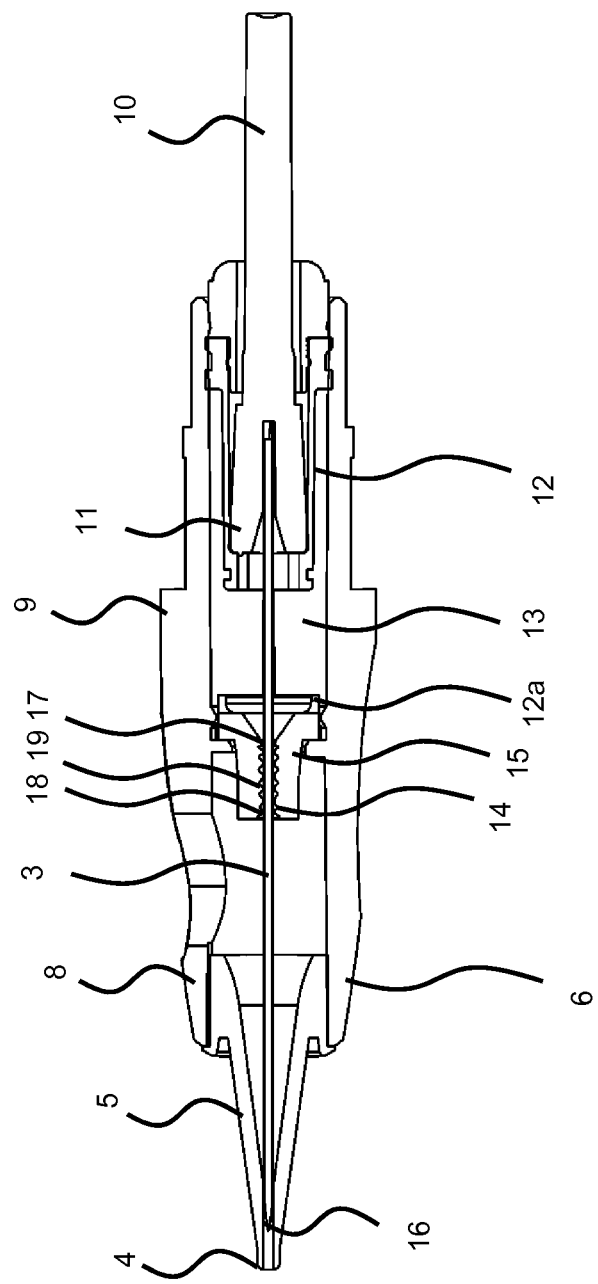
FIG. 2 shows a schematic illustration of a needle module, in the case of which a needle-guiding component is arranged in the housing of the needle module.

FIG. 2 shows a needle module 6 comprising a needle module housing 9, in which the skin pricking needle 3 is arranged, which is received on the rear side of a needle shaft 10. The needle shaft 10 is received with a front section 11 in an elastic membrane 12. The elastic membrane 12 seals an interior 13 in the needle module housing 9 against the needle shaft 10 and the space receiving said needle shaft.

The skin pricking needle 3 is guided along a needle channel 14 in a needle-guiding component 15 and escapes with at least one needle tip 16 through the needle nozzle opening 4 on the needle or module nozzle 5 in response to moving forward and backward.

Figure 3:
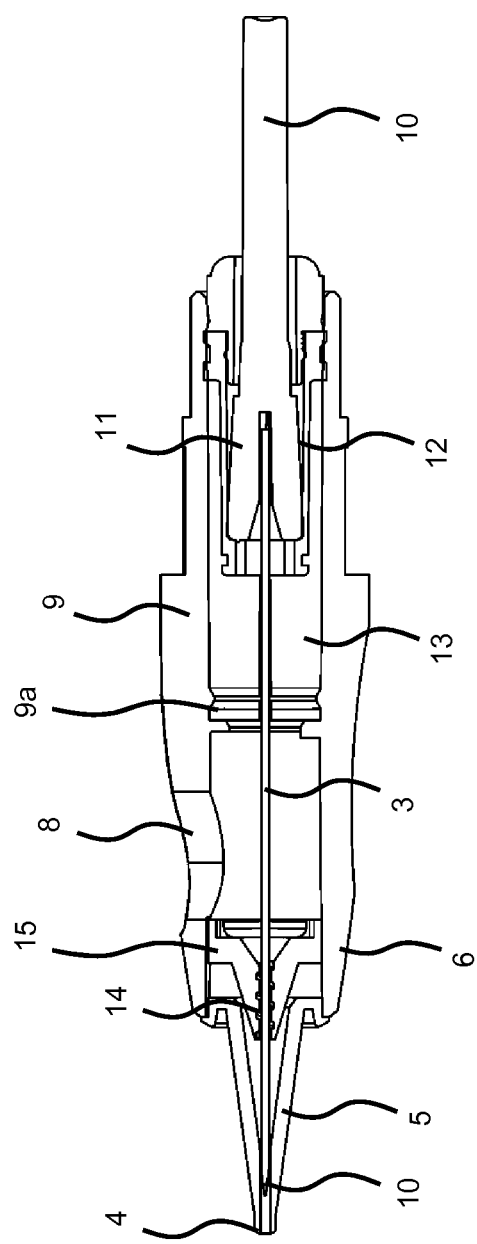
FIG. 3 shows a schematic illustration of a needle module, in the case of which the needle-guiding component is arranged closer to the module tip.

FIG. 3 shows a schematic illustration of a needle module 6, in the case of which the needle-guiding component 15 is arranged on a rear side of the needle nozzle 5 adjacently thereto and partially engages with the needle nozzle 5.

The needle channel 14, which has proximal guide wall sections 18 and distal wall sections 19 on a channel wall 17, is formed in the needle-guiding component 15. In response to moving the skin pricking needle forward and backward, the latter is guided by means of the proximal guide wall sections 18 such that the proximal guide wall sections potentially come into direct contact with the skin pricking needle, so that the skin pricking needle is guided through here. Distal wall sections 19, which are recessed, in contrast, are provided between the proximal guide wall sections 18. The skin pricking needle does not come to rest against them in the movement. Volumes 20, which can potentially serve to receive a fluid, which is discharged through the needle opening 4, are instead formed between the skin pricking needle and the distal wall sections 19.

The skin pricking needle 3 is additionally guided on a housing section 9a in the needle module 6.

In the design in FIG. 2, the needle-guiding component 15 is arranged rearward with respect to the opening 8, while it is arranged between needle opening 4 and opening 8 in the case of the design in FIG. 3. When a fluid, which is to be applied to the skin, is introduced via the opening 8, said fluid is transported through the fluid channel 14 in the case of the design in FIG. 3, in particular due to the back and forth movement of the skin pricking needle 3, in order to finally reach the needle opening 4. In particular in the case of this embodiment, the needle channel 14 is then formed as a fluid-transporting channel.

Figure 4:
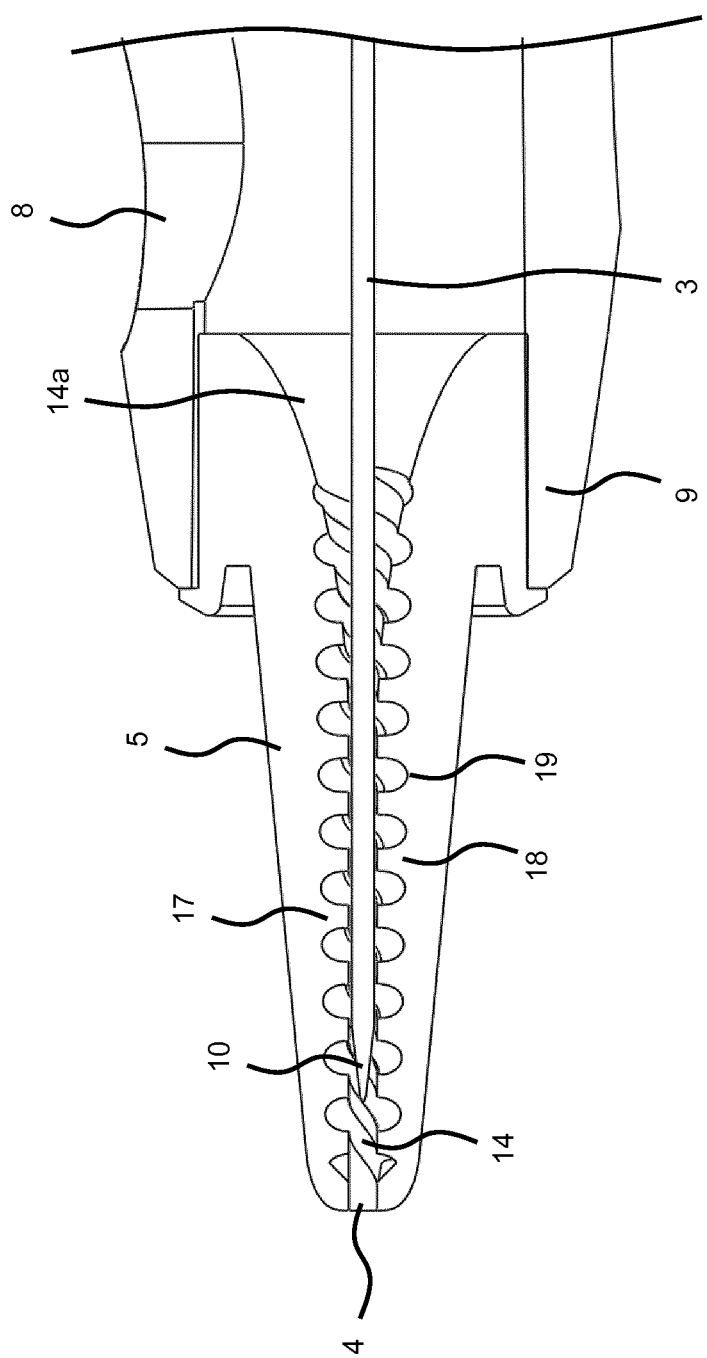
FIG. 4 shows a front section of a needle module comprising a needle channel in a needle nozzle, wherein a skin pricking needle is retracted.
Figure 5:
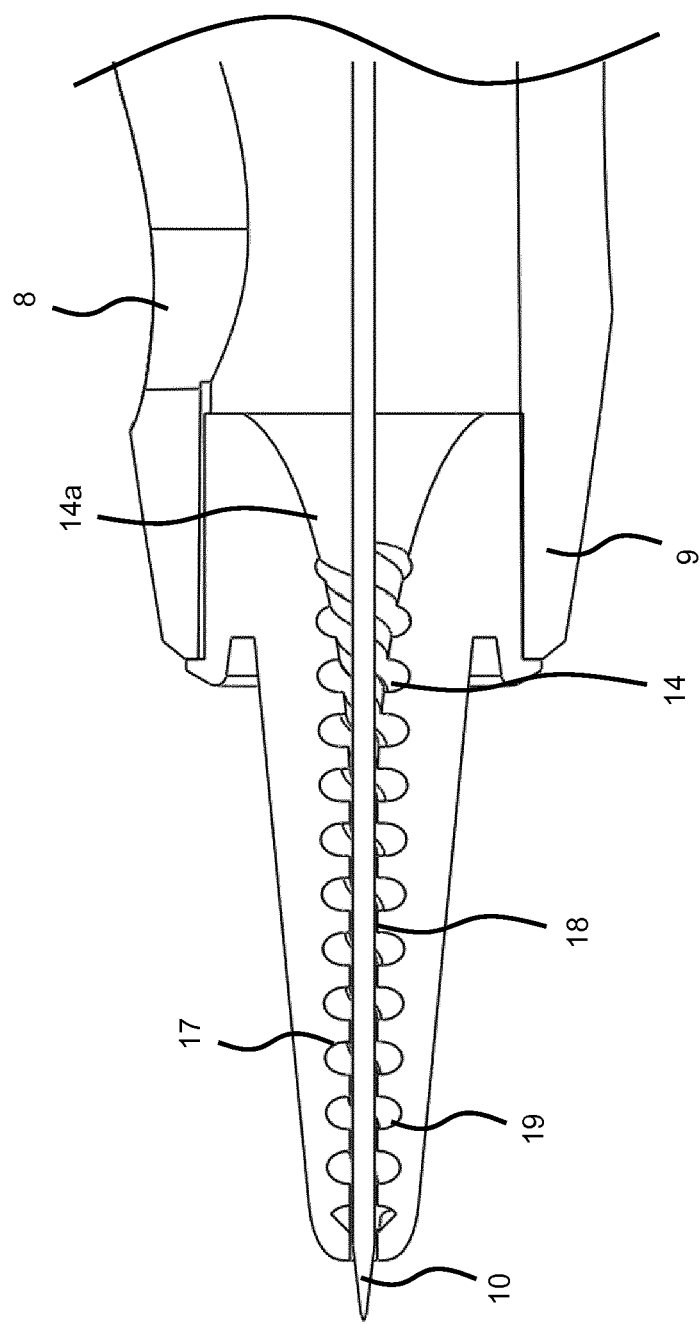
FIG. 5 shows a further schematic illustration of the arrangement from FIG. 4, wherein the needle tip of the skin pricking needle is extended.
Figure 6:
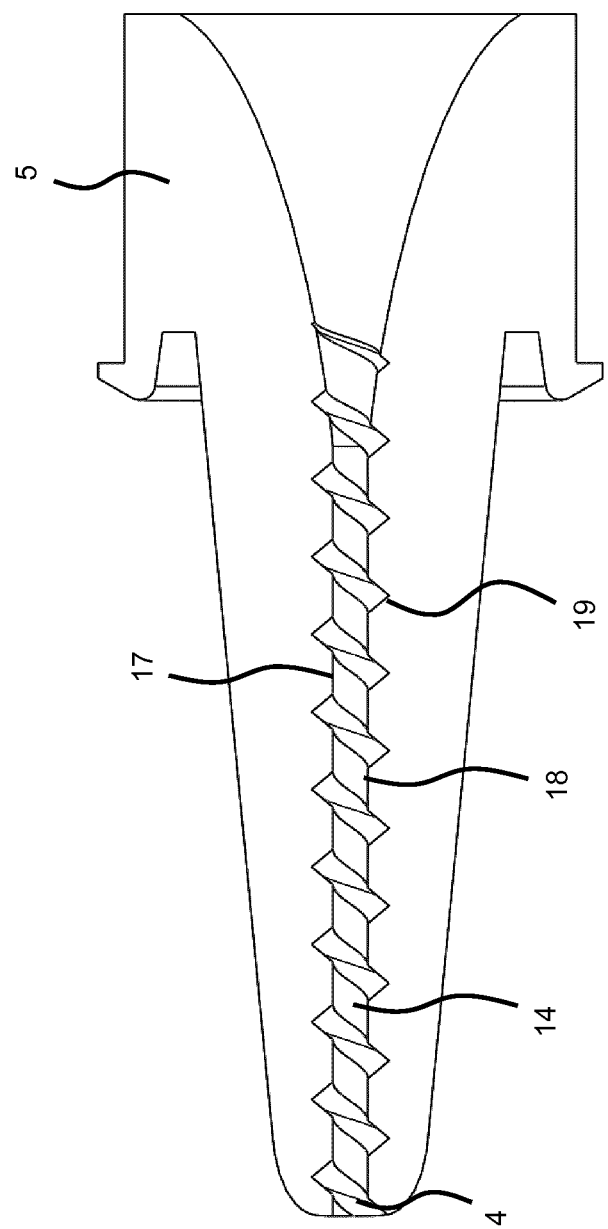
FIG. 6 shows a schematic illustration of a needle nozzle comprising a needle channel.

FIGS. 4 and 5 show a front section of the needle module 6, wherein the needle channel 14 is formed in the needle nozzle 5, which is formed here so as to provide the needle-guiding component 15. A widening, which connects to the needle channel 14 on the rear side, is arranged in a rearward section 14a.

FIGS. 6 to 9 show embodiments of the needle nozzle 5 comprising a differently embodied needle channel 14.

Figure 7:
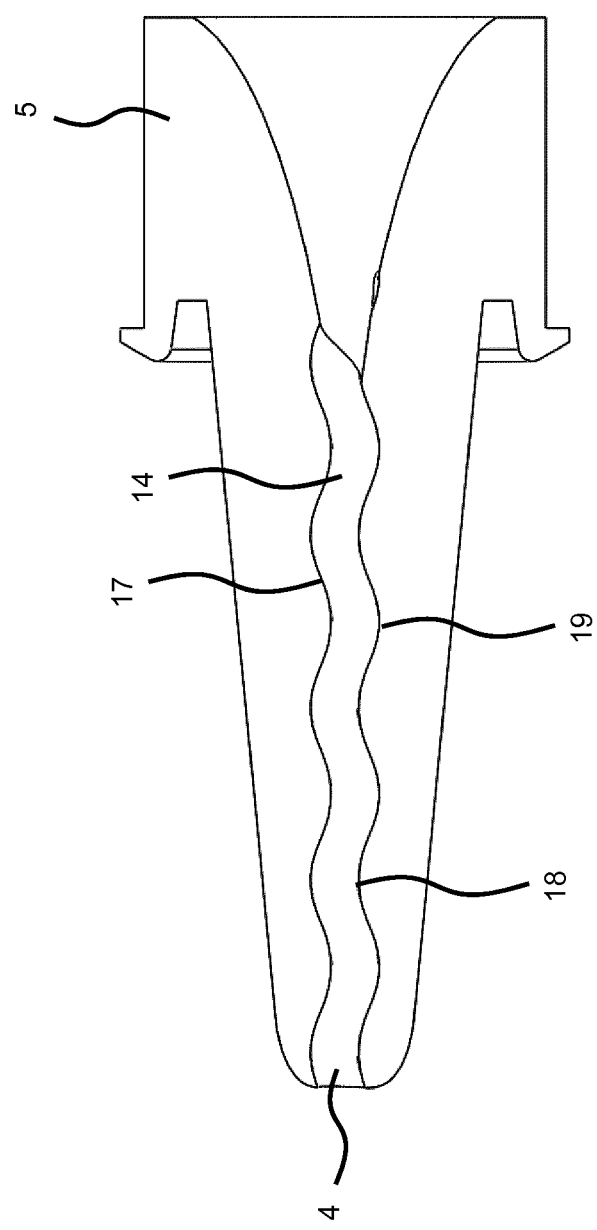
FIG. 7 shows a schematic illustration of a further needle nozzle comprising needle channel.
Figure 8:
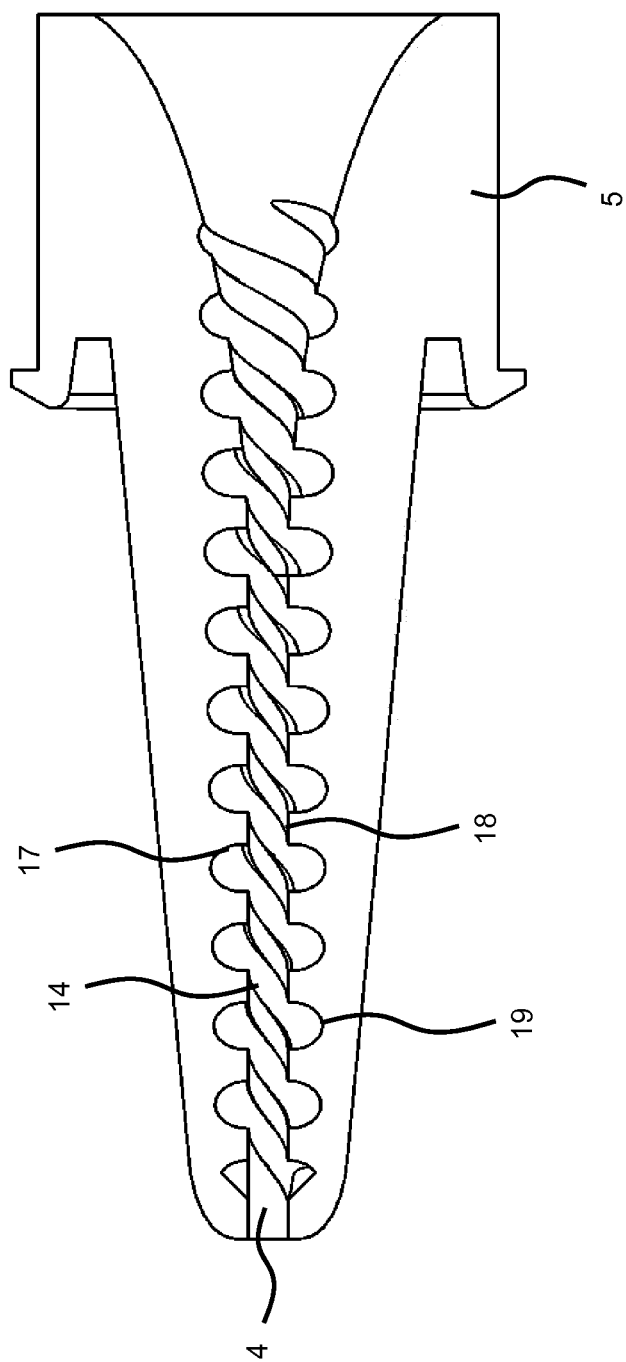
FIG. 8 shows a schematic illustration of another needle nozzle comprising needle channel.
Figure 9:
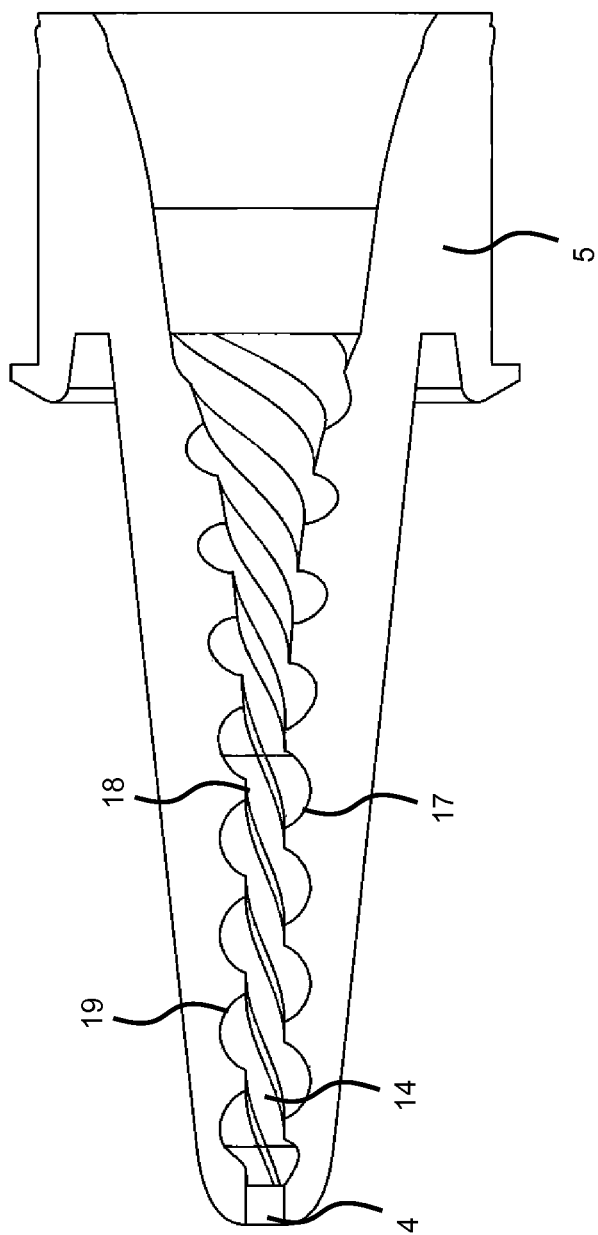
FIG. 9 shows a schematic illustration of a further needle nozzle comprising needle channel.

In the case of the embodiments in FIGS. 4 to 9, the proximal guide wall sections 18 and/or the distal wall sections 19 are formed along circumferential spiral lines, which can be designed as helical line. FIG. 7 shows an embodiment, in the case of which the channel wall 17 of the needle channel 14 is formed with a waveform, for example a sinusoidal waveform. In the case of the design in FIG. 9, the incline changes along the needle channel 14, i.e. a spiral line comprising a changing incline is provided there.

Figure 10:
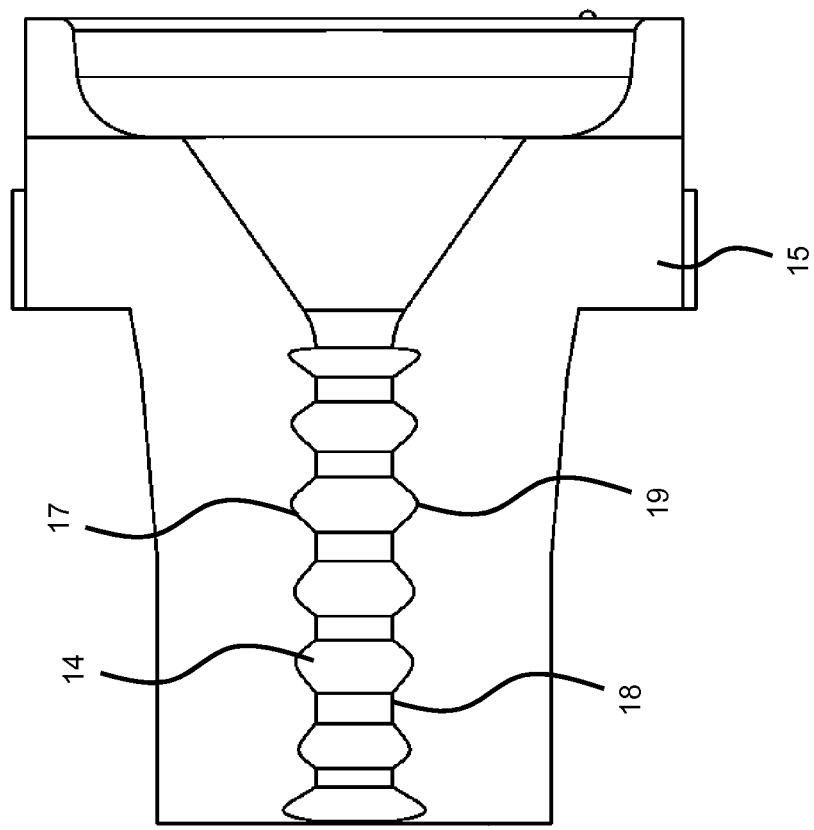
FIG. 10 shows a schematic illustration of a needle-guiding component comprising needle channel.
Figure 11:
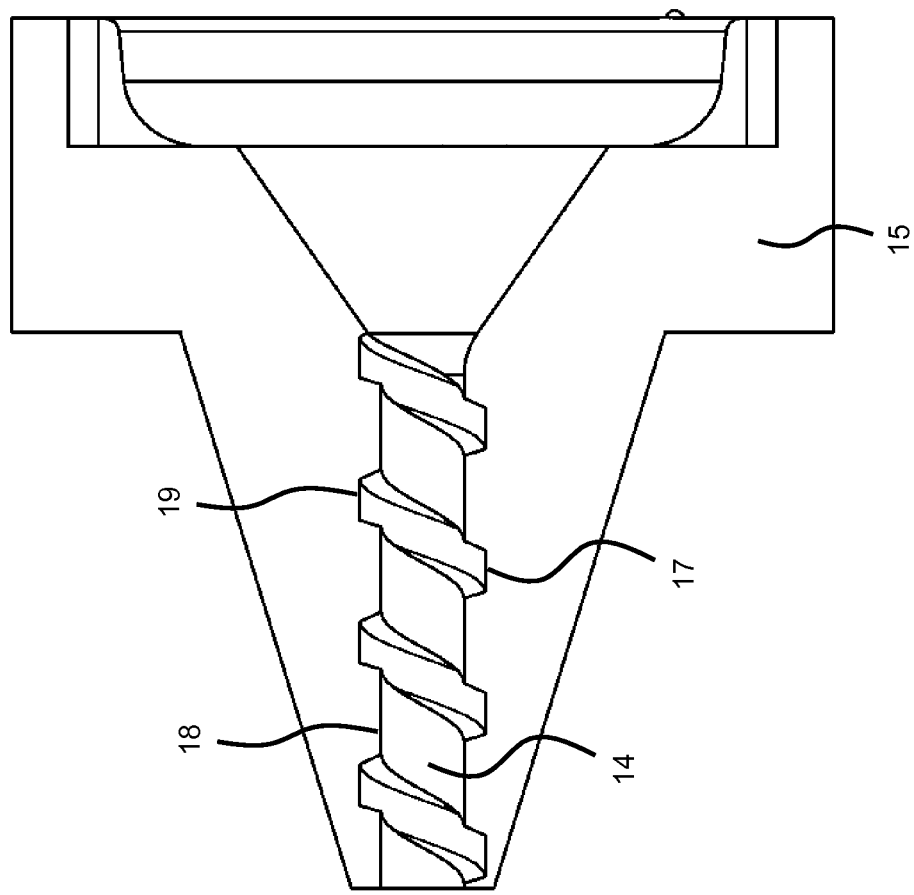
FIG. 11 shows a schematic illustration of a further needle-guiding component comprising needle channel.

FIGS. 10 and 11 show embodiments of the needle-guiding component 15, which is arranged to form the needle channel 14 in the needle module 6, for example corresponding to the embodiments in FIG. 2 or 3.

Figure 12:
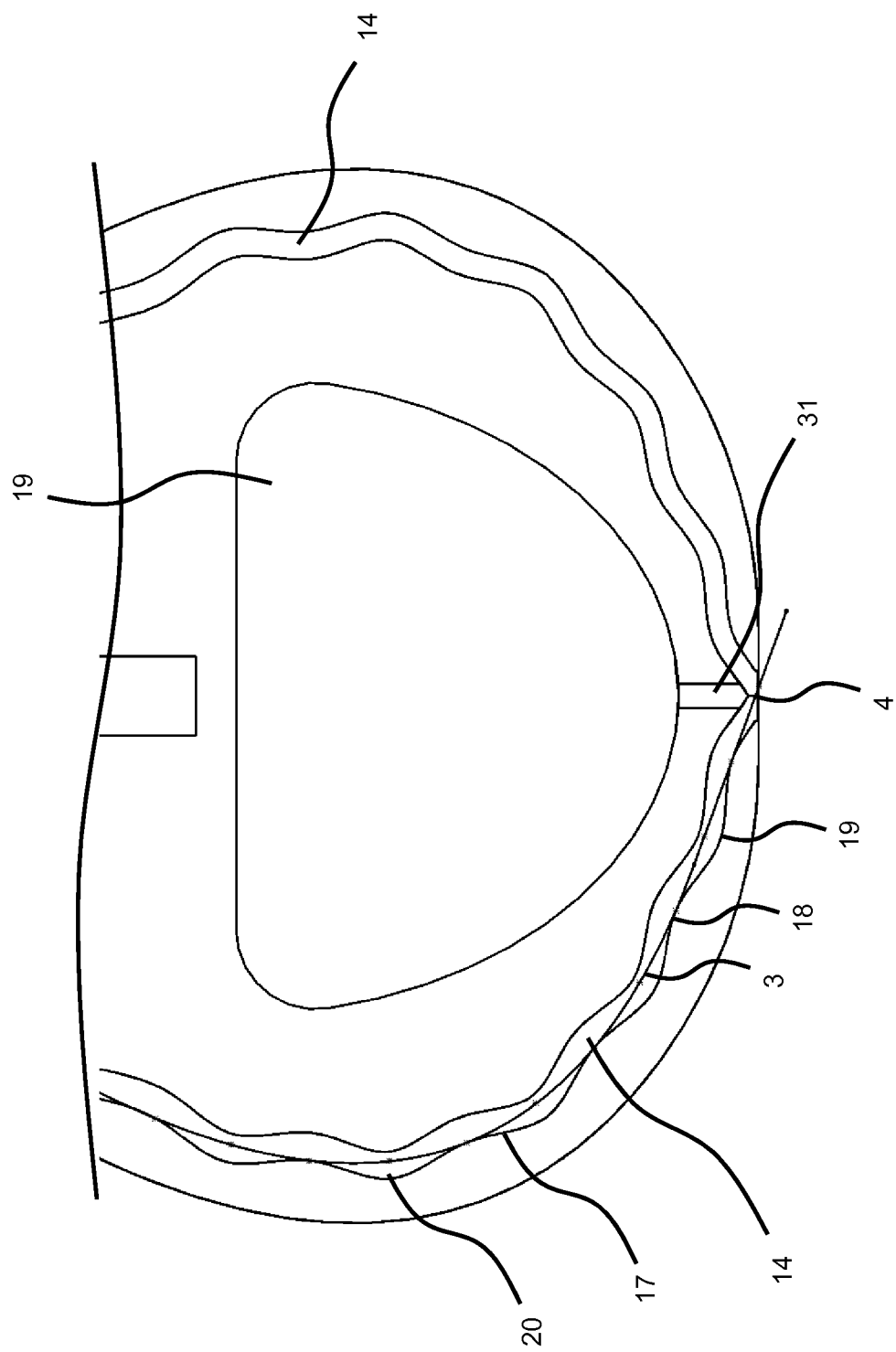
FIG. 12 shows a schematic illustration of a front section of a needle module for a flat or a round needle.
Figure 13:
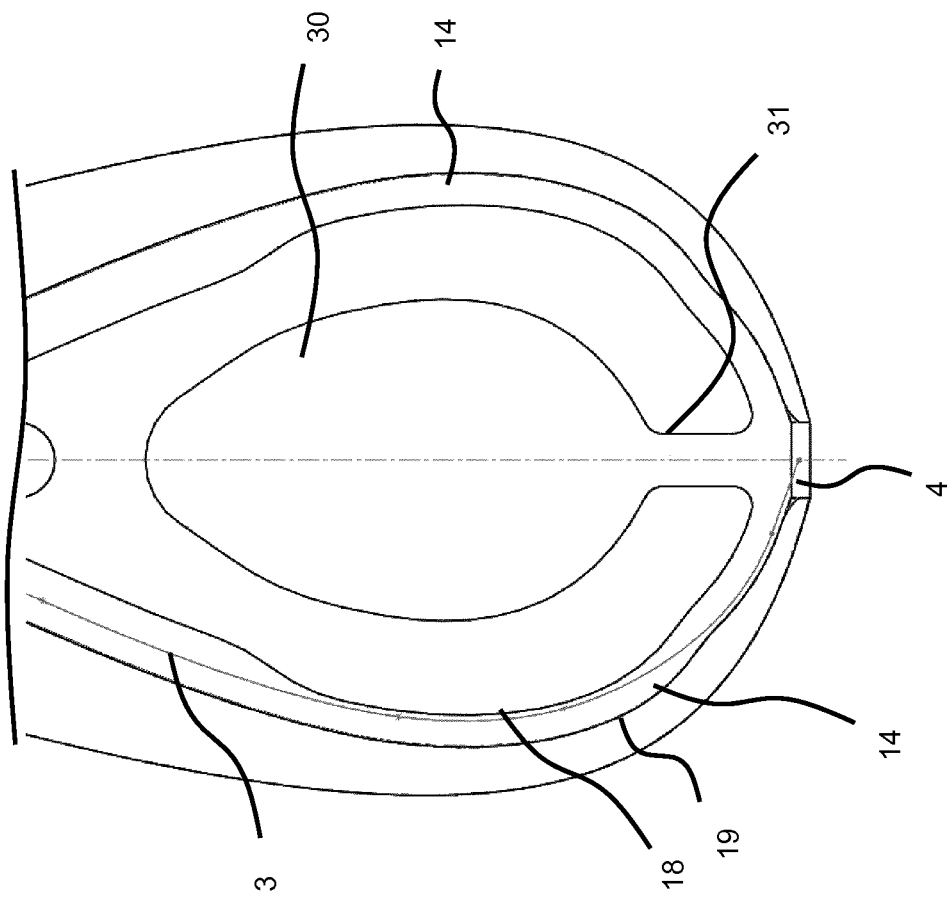
FIG. 13 shows a schematic illustration of a front section of a further needle module for a flat or a round needle.

FIGS. 12 and 13 show a front section of a needle module 6, in the case of which the needle channel 14 is formed on both sides of a fluid reservoir 30. The skin pricking needle 3, which has for example a flat profile in the cross section, is arranged in the needle channel. The needle opening 4 is in fluid communication with the fluid reservoir 30 via a fluid channel 31.

Figure 14:
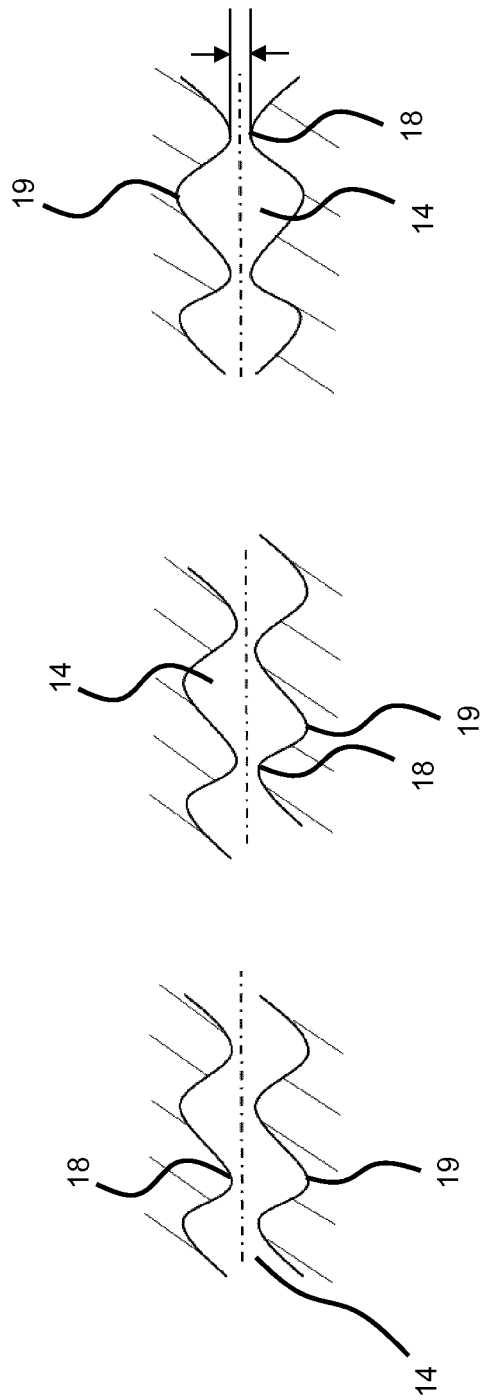
FIG. 14 shows a schematic illustration of needle channels in cross section.
Figure 15:
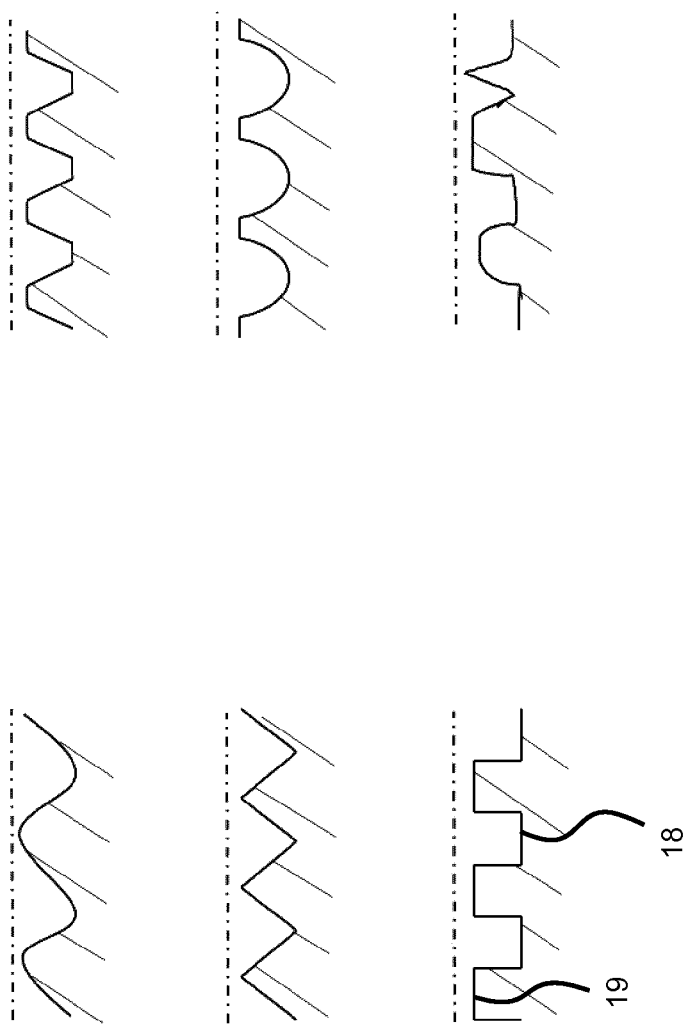
FIG. 15 shows schematic illustrations of sections of a needle channel.

FIGS. 14 to 16 show further embodiments for the needle channel 14. An effective channel width is determined by the distance at right angles to the longitudinal direction of the needle channel 14 between the proximal guide wall sections 18 arranged on opposite sides. Different cross-sectional shapes can be provided, for example round or angular.

An effective channel width B (in the sectional illustration) of the needle channel 14, which is determined by a distance at right angles to the longitudinal direction of the needle channel 14 of proximal guide wall sections 18 on opposite sides of the needle channel 14 (see FIG. 14), can be larger than a thickness of the skin pricking needle 3, in particular such that a smooth moving of the skin pricking needle 3 in the needle channel 14 is at hand, in particular also when the fluid is transported along the needle channel 14. The effective channel width can be consistent across the length of the needle channel 14. In the alternative, the effective channel width can change over the length of the needle channel 14.

FIG. 14 further shows (in the sectional illustration) a width C of a discharged volume of the fluid in a schematic manner.

Figure 17:
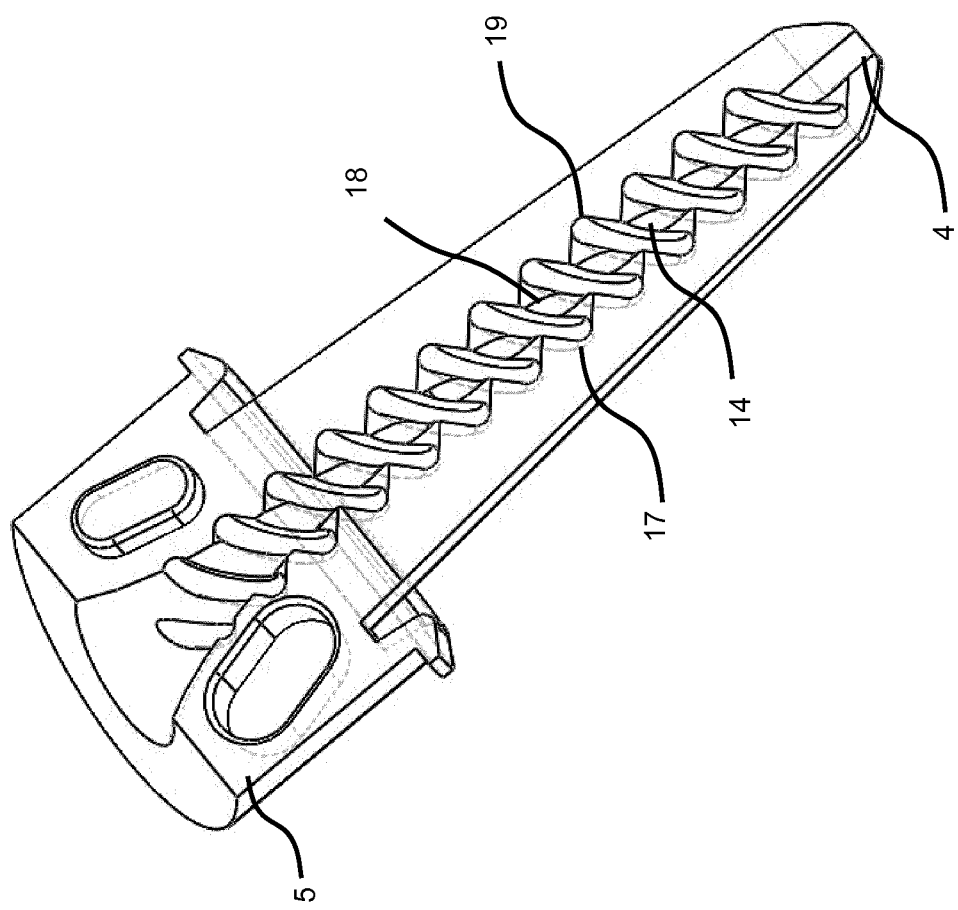
FIG. 17 shows a schematic perspective illustration of a needle nozzle comprising a needle channel, in the case of which guide sections are arranged along a spiral line.
Figure 18:
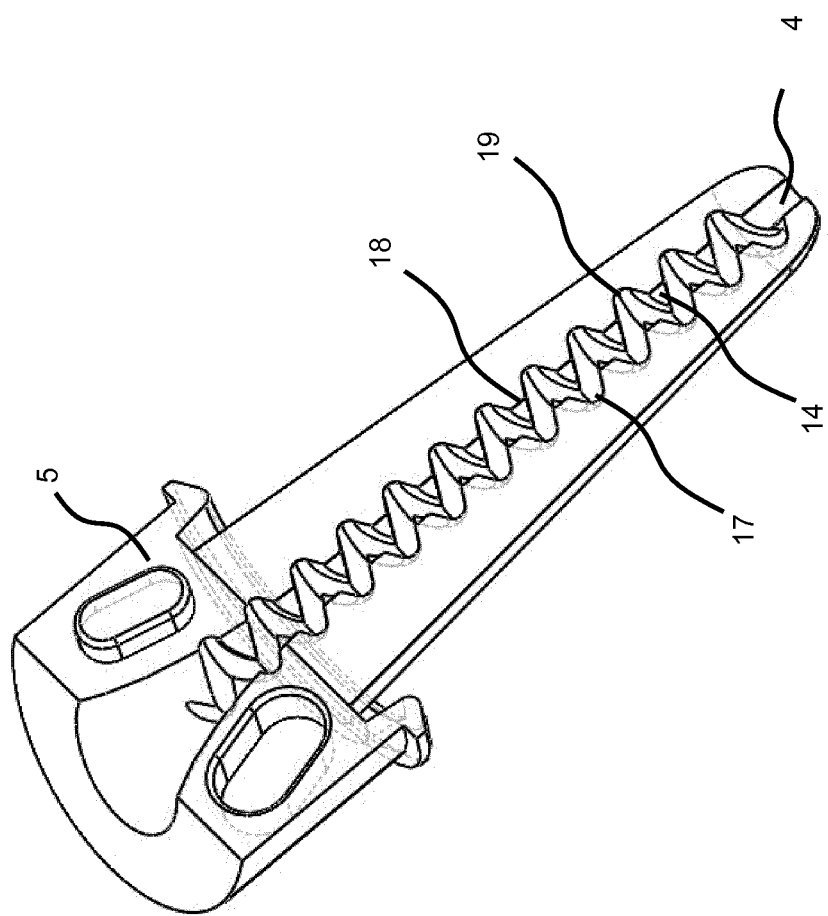
FIG. 18 shows a schematic perspective illustration of a further needle nozzle comprising a needle channel, in the case of which guide sections are arranged along a meander-like line.

FIGS. 17 and 18 in each case show a schematic perspective illustration of designs of the needle nozzle 5 comprising needle channel 14, wherein the proximal guide wall sections 18 and/or the distal wall sections 19 are arranged along a spiral line (FIG. 17) or along a meander-like line (FIG. 18).

Figure 19:
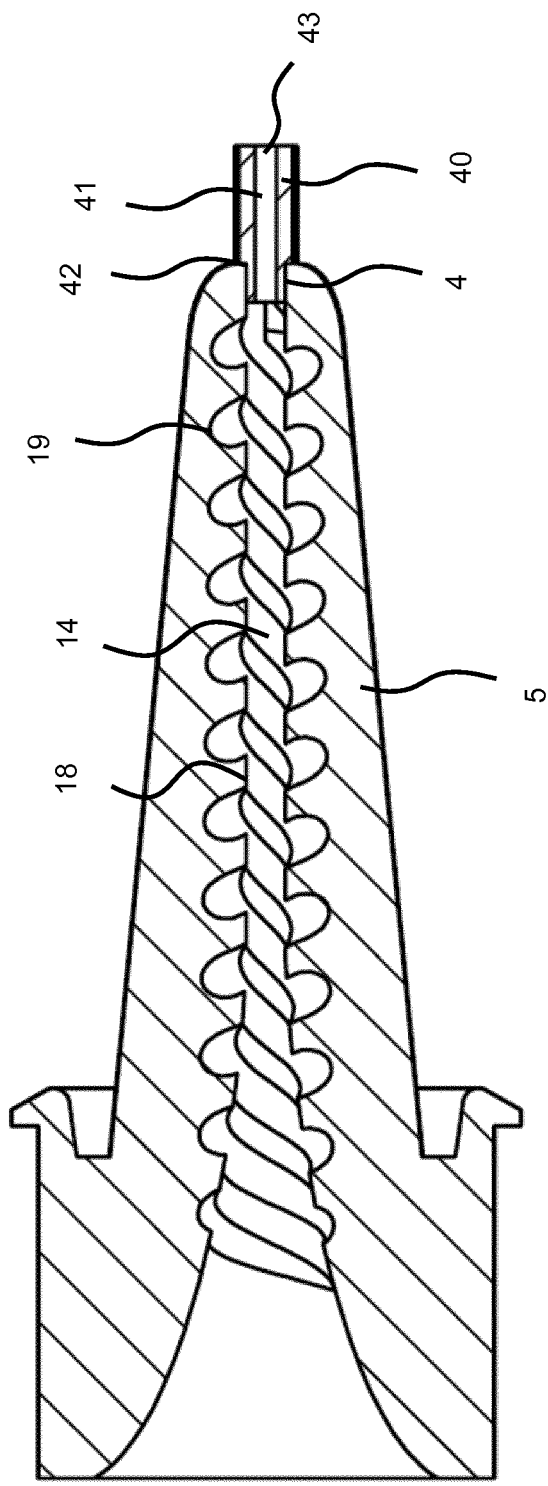
FIG. 19 shows a schematic illustration of an alternative embodiment of a needle nozzle.

FIG. 19 shows an alternative embodiment of the needle nozzle 5, in the case of which a needle-guiding element 40 is arranged in the area of the needle opening 4, which needle-guiding element, in the shown design, is designed in an exemplary manner as attachment or top piece and in which the skin pricking needle 3 (not illustrated) is guided in an extension 41 of the needle channel 14 in response to moving forward and backward. The needle-guiding element 40 sticks out from the needle nozzle 5 and is inserted or plugged into the needle opening 4 with a proximal end 42 in the shown embodiment. In the alternative, the proximal end 42 can be attached to the needle-guiding element 40 or can be integrally molded to the needle nozzle 5. An outlet opening 43 for the skin pricking needle 3 is thus arranged offset to the needle opening 4. In the case of the shown design, the needle-guiding element 40 is formed to be free from proximal guide wall sections 18 and distal wall sections 19.

Figure 20:
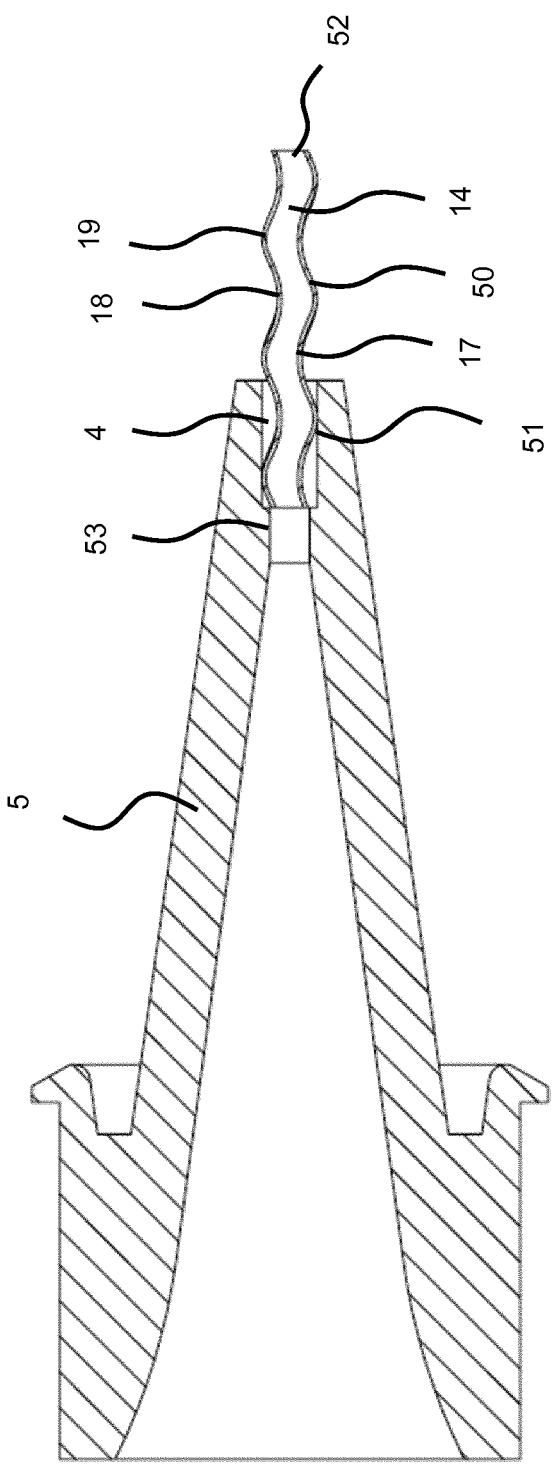
FIG. 20 shows a schematic illustration of a further alternative embodiment of a needle nozzle.

FIG. 20 shows a further alternative embodiment of the needle nozzle 5, in the case of which a needle-guiding element 50 is arranged in the area of the needle opening 4, which needle-guiding element can be designed as attachment piece, insert or top piece and in which the skin pricking needle 3 is guided in the needle channel 14 in response to moving forward and backward. The needle-guiding element 50 sticks out to the front or protrudes from the needle nozzle 5 and is inserted into the needle opening 4 with a proximal end 51 in the case of the shown embodiment. In the alternative, the needle-guiding element 50 can be attached. A one-piece design with the needle nozzle 5 can be provided as well. In the area of the channel wall 17, the proximal guide wall sections 18 and the distal wall sections 19 are formed along the needle channel 14 on the needle-guiding element 50. An outlet opening 52 for the skin pricking needle 3 is arranged offset to (upstream of) the needle opening 4. A guide section 53, which connects to the needle-guiding element 50, is arranged on the rear side in the section comprising the needle opening 4. In the alternative, a distance can be provided therebetween.

The features disclosed in the above description, the claims as well as the drawing can be significant alone as well as in any combination for the realization of the different designs.

The invention claimed is:

1. A needle-guiding device for a skin pricking device (1), comprising
a base body;
a skin pricking needle (3);
a needle channel (14), which is formed in the base body and in which the skin pricking needle (3) is provided, wherein the skin pricking needle (3) can be moved back and forth repeatedly in the needle channel (14) along a movement path,
wherein a channel wall (17) of the needle channel (14) has proximal guide wall sections (18) with respect to the skin pricking needle (3), on which the skin pricking needle (3) comes to rest for needle guidance in response to the back and forth movement, and has distal wall sections (19), which are recessed relative to the proximal guide wall sections (18) and which are free from a direct contact with the skin pricking needle (3) in response to moving the skin pricking needle (3) back and forth in the needle channel (14); and
a fluid is transported in a flowing manner in a spiral fluid transport channel running around the needle channel (14) and provided by the proximal guide wall sections (18) and the distal wall sections (19) extending completely around the skin pricking needle (3).

2. The needle-guiding device according to claim 1, wherein the proximal guide wall sections (18) and the distal wall sections (19) are formed alternately along the movement path in the needle channel (14).

3. The needle-guiding device according to claim 1, wherein the formation of the proximal guide wall sections (18) and of the distal wall sections (19) are limited to a partial area of a periphery of the channel wall (17) encompassing the needle channel (14).

4. The needle-guiding device according to claim 1, wherein the proximal guide wall sections (18) and/or the distal wall sections (19) are arranged along one or a plurality of spiral lines each running around the needle channel (14) to form the spiral fluid transport channel.

5. The needle-guiding device according to claim 1, wherein voids (20) are formed between the skin pricking needle (3) and the distal wall section (19) and are in fluid communication along the movement path and are configured to receive fluid.

6. The needle-guiding device according to claim 1, wherein the movement path has a straight section in a straight needle channel section and/or a curved section in a curved needle channel section.

7. The needle-guiding device according to claim 1, wherein the proximal guide wall sections (18) have a flat and/or a punctiform contact surface such that, in response to guiding the skin pricking needle (3) in the needle channel (14), said skin pricking needle forms a flat and/or a punctiform direct contact with the proximal guide wall section (18).

8. The needle-guiding device according to claim 1, wherein the proximal guide wall sections (18) and/or the distal wall sections (19) are formed offset to one another in channel wall sections located opposite one another along the movement path.

9. The needle-guiding device according to claim 1, wherein the needle channel (14) is connected to a fluid reservoir (30).

10. The needle-guiding device according to claim 1, wherein an effective channel width of the needle channel (14), which is determined by a distance at right angles to the longitudinal direction of the needle channel (14) of proximal guide wall sections (18) on opposite sides of the needle channel, is larger than a thickness of the skin pricking needle (3).

11. The needle-guiding device according to claim 1, wherein the needle channel (14) is at least partially formed in a needle nozzle (5).

12. A skin pricking device, comprising a drive module (7) and a needle module (6) coupled thereto, wherein the needle module (6) has a needle-guiding device according to claim 1.

13. The needle-guiding device according to claim 1, wherein the base body is designed as a disposable component with the needle channel (14).

14. The skin pricking device according to claim 12, wherein the needle channel (14) is at least partially formed in a needle-guiding component (15) of the needle module (6).

\* \* \* \* \*